(12) United States Patent
Eliachar et al.

(10) Patent No.: US 7,300,447 B2
(45) Date of Patent: Nov. 27, 2007

(54) WORKING TOOL FOR ACCURATE LATERAL RESECTION OF BIOLOGICAL TISSUE AND A METHOD FOR USE THEREOF

(75) Inventors: Eli Eliachar, Haifa (IL); Ofer Yossepowitch, Tiqvah (IL)

(73) Assignee: Roei Medical Technologies Ltd., Katzrin (IL)

( * ) Notice: Subject to any disclaimer, the term of this patent is extended or adjusted under 35 U.S.C. 154(b) by 149 days.

(21) Appl. No.: 10/514,445

(22) PCT Filed: May 14, 2003

(86) PCT No.: PCT/IL03/00389

§ 371 (c)(1),
(2), (4) Date: Nov. 15, 2004

(87) PCT Pub. No.: WO03/096912

PCT Pub. Date: Nov. 27, 2003

(65) Prior Publication Data

US 2005/0171531 A1 Aug. 4, 2005

(30) Foreign Application Priority Data

May 15, 2002 (IL) .................................. 149689

(51) Int. Cl.
*A61B 17/32* (2006.01)
*A61B 1/018* (2006.01)

(52) U.S. Cl. .................. 606/170; 606/46; 606/169; 600/104

(58) Field of Classification Search .......... 606/167, 606/169–171, 176–180, 46; 128/898; 604/22; 600/104–107, 112, 114
See application file for complete search history.

(56) References Cited

U.S. PATENT DOCUMENTS

| | | | |
|---|---|---|---|
| 5,571,085 A | 11/1996 | Accisano | |
| 5,622,078 A | 4/1997 | Mattson | |
| 3,049,018 A * | 8/1962 | Lusskin et al. | 74/89.45 |
| 3,952,604 A | 4/1976 | Baudler | |
| 4,000,664 A | 1/1977 | Christensen | |
| 4,282,442 A | 8/1981 | Massinger | |
| 4,912,995 A | 4/1990 | Otters | |
| 4,973,334 A | 11/1990 | Ziemann | |
| 5,133,713 A * | 7/1992 | Huang et al. | 606/46 |
| 5,134,923 A | 8/1992 | Wexler | |
| 5,176,677 A * | 1/1993 | Wuchinich | 606/46 |
| 5,269,757 A | 12/1993 | Fagan et al. | |
| 5,281,220 A * | 1/1994 | Blake, III | 606/46 |
| 5,358,479 A | 10/1994 | Wilson | |
| 5,419,237 A | 5/1995 | Jeppsson | |
| 5,472,439 A * | 12/1995 | Hurd | 606/1 |
| 5,483,929 A | 1/1996 | Kuhn et al. | |
| 5,505,693 A * | 4/1996 | Mackool | 604/22 |

(Continued)

FOREIGN PATENT DOCUMENTS

EP 1183990 A2 3/2002

*Primary Examiner*—Glenn K. Dawson
*Assistant Examiner*—Kathleen Sonnett
(74) *Attorney, Agent, or Firm*—Browdy and Neimark, PLLC

(57) ABSTRACT

The present invention provides a novel and most useful working tool for a resectoscope, adapted to side-to-side resection of biological tissue using predetermined lateral movement. Said resectoscope is adapted to either cold or hot resection and is either flexible or rigid. The present invention also provides for a suitable cutting member assembly and to a method useful for lateral resection.

6 Claims, 16 Drawing Sheets

U.S. PATENT DOCUMENTS

| | | |
|---|---|---|
| 5,631,514 A | 5/1997 | Garcia et al. |
| 5,702,420 A * | 12/1997 | Sterling et al. ............. 606/205 |
| 5,746,093 A | 5/1998 | Poglitsch |
| 5,746,760 A | 5/1998 | Humphrey, Jr. |
| 5,925,056 A * | 7/1999 | Thomas et al. ............. 606/180 |
| 5,935,143 A * | 8/1999 | Hood ......................... 606/169 |
| 6,036,698 A * | 3/2000 | Fawzi et al. ................ 606/114 |
| 6,161,733 A | 12/2000 | King |
| 6,231,027 B1 | 5/2001 | Baker et al. |
| 6,244,228 B1 | 6/2001 | Kuhn et al. |
| 6,296,639 B1 * | 10/2001 | Truckai et al. ................ 606/41 |
| 6,508,805 B1 | 1/2003 | Garabedian et al. |
| 6,575,970 B2 * | 6/2003 | Quick ........................ 606/45 |
| 6,663,596 B2 | 12/2003 | Griego et al. |
| 6,676,658 B2 * | 1/2004 | Burbank et al. ............... 606/45 |
| 6,971,989 B2 * | 12/2005 | Yossepowitch ............. 600/105 |
| 2001/0029372 A1 | 10/2001 | Quick |
| 2001/0048265 A1 | 12/2001 | Miller et al. |
| 2002/0010485 A1 | 1/2002 | Griego et al. |
| 2003/0060842 A1 | 3/2003 | Chin et al. |
| 2004/0030350 A1 | 2/2004 | Griego et al. |
| 2004/0064139 A1 | 4/2004 | Yossepowitch |

* cited by examiner

WORKING TOOL FOR ACCURATE LATERAL RESECTION OF BIOLOGICAL TISSUE AND A METHOD FOR USE THEREOF

FIELD OF THE INVENTION

The present invention relates to a working tool for accurate lateral resection of biological tissue and for a method for using the same.

CROSS-REFERENCE TO RELATED APPLICATIONS

This application is a U.S. National Phase Application under 35 U.S.C. 371 of PCT International Application No. PCT/IL2003/00389, which has an international filing date of May 14, 2003, and which claims priority from Israel Patent Application No. 149,689, filed May 15, 2002.

BACKGROUND OF THE INVENTION

Resectoscopes are medical devices useful for the resection of biological tissue, usually in order to remove pathologies in the tissue or to sample suspect tissue. Resectoscopes are elongated, narrow devices, which penetrate mammalian cavities. Typically, the resectoscope's distal end is positioned in the cavity and its proximal end is located outside the body. Resectoscopes comprise inter alia an elongated optical system and an actuator, wherein the actuator has means to translate a movement of at least one handle along the longitudinal axis of the resectoscope to the movement of a resecting loop, wherein the loop is connected to an electrical source and thus has means to resect the desired tissue along the longitudinal axis.

All resectoscopes known in the art comprise a cutting member, wherein cutting is enabled by means of an electrical current, which produces sufficient heat to coagulate and cut tissue. The heat burns the resected tissues so further analysis of the tissue is impaired.

The user of resectoscopes known in the art determines the depth of cutting beneath the tissue mucosa. The more the user presses the resectoscope against the tissue, the deeper the resection. However, resection using motion along the longitudinal axis provides no reference to guide the user as to the necessary depth of resection. Resection therefore often depends mainly on the user's sensitivity, experience and technical skills. In order to avoid penetration of organs and contamination of the body with diseased tissue, thereby introducing complications to the surgical procedure, users avoid pressing the resectoscope. Most procedures therefore yield inefficient resection depth and therefore inaccurate pathological staging. Moreover, due to technical characteristics of the aforementioned endoscopic resection, specimens are often found excessively cauterized and inappropriate for accurate pathological diagnosis. Likewise, technical disadvantages of the aforementioned endoscopic resection prevent the complete removal of the tumor tissue. Herr et al. demonstrated that up to 76% of the patients with bladder tumors have residual tumors after an initial resection, and 30% of the patients were inaccurately downstaged at initial trans-urethral resection. They therefore advocate routine repeat resection for every patient to control noninvasive tumors and to detect residual tumor invasion (J. Urol. July 1999; 1 62(1): 74-6).

Prior art resectoscopes, their method of use, and ancillary systems usable with them are discussed in PCT application WO 0172200, filed Mar. 29, 2001, assigned to the present applicant and incorporated herein by reference in its entirety.

SUMMARY OF THE INVENTION

It is thus an object of the present invention to present an accurate working tool for resectoscopes for lateral, side to side resection of biological tissue, a resectoscope including such a working tool, and a method for using such a working tool. Cutting member assemblies and cutting members suitable for lateral resections are also provided in the present invention. In embodiments of the present invention, vibratory or oscillatory motion is applied by a means for vibration to the cutting member assembly as the assembly rotates.

There is thus provided in accordance with a preferred embodiment of the present invention a working tool for a resectoscope for side-to-side resection of biological tissue using predetermined lateral movement. The working tool has a distal end, which is inserted into a body cavity, a proximal end that is adjacent to a user, and a longitudinal axis. The tool also includes:

a rotation mechanism which includes:
 a handle assembly located at the proximal end of the tool, the assembly including at least two handles, one or more handles being movable in the longitudinal direction of the tool; and
 a drive screw in communication via a cam element with the handle assembly, the drive screw positioned along the longitudinal axis and rotatable around that axis upon a predetermined translation of the one or more movable handles, the translation transformed to a rotation by the cam element; and
one or more cutting member assemblies positioned at the distal end of the tool, each of the assemblies including:
 a cutting member axle connected by one or more connecting elements to the drive screw, the cutting member axle thereby being rotatable upon rotation of the drive screw; and
 one or more cutting members connected to and positioned at an end of the cutting member axle distal from the drive screw, the one or more cutting members, when held in a predetermined position with respect to tissue to be resected, being operable to rotate and resect tissue to a predetermined depth in a substantially side-to-side manner upon rotation of the cutting member axle.
 There is provided in another embodiment of the working tool of the present invention, a cutting member axle which is rotatable about the longitudinal axis in predetermined arcs of less than 360°. In another embodiment of the working tool, there is provided a cutting member axle which is rotatable around said longitudinal axis in rotations of 360° or more.

In yet another embodiment of the present invention, the working tool further includes one or more vibrators, the vibrators being in communication with the cutting member axle, vibrating the cutting member axle along the longitudinal axis (x-axis). In yet another embodiment, the vibrators vibrate the cutting member axle as the cutting member rotates around the longitudinal axis.

Additionally, in another preferred embodiment of the present invention, the one or more vibrators of the working tool includes a motor, which has an eccentric pin positionable in a slot in a linear actuator, thereby affixed to the actuator. The linear actuator additionally includes one or more female slot-like recesses, which are spaced and dimensioned to fit one or more male members located on the cutting member axle, thereby affixing the actuator to the cutting member axle. In some embodiments of the invention, the vibrator's motor is selected from a group consisting of an AC electrical motor, a DC electrical motor, a hydraulic motor and a pneumatic motor. In yet other embodiments, the one or more vibrators of the working tool can be selected from one of several electrical means, such as piezoelectric and crystal oscillators, and ultrasound generators.

In yet another embodiment of the present invention, the cutting member of the working tool is connected to the cutting member axle at one or more points.

In an additional embodiment of the present invention, the drive screw of the working tool is anchored within the working tool by one or more locks. In another embodiment, the drive screw of the working tool rotates without advancing longitudinally. In yet another embodiment, the one or more connecting element connects the cutting member axle to the drive screw by properly spaced and dimensioned matable male and female members on the axle and screw.

Additionally, in a further preferred embodiment of the present invention, the working tool has a chassis fitted with one or more snap-in elements positioned along the chassis's length. The cutting member axle is positioned and held within the one or more snap-in elements and the cutting member axle is free to rotate around the tool's longitudinal axis (x-axis). In a further preferred embodiment of the present invention, the working tool has a chassis fitted with one or more snap-in elements positioned along the chassis's length. The cutting member axle is positioned and held within the one or more snap-in elements and the cutting member axle is free to rotate around the tool's longitudinal axis (x-axis) and translate along the longitudinal axis.

In another embodiment of the present invention, the one or more snap-in elements includes a groove with a female notch-like recess and where the cutting member includes a male protruding member suitably sized and positioned for mating with the groove's notch-like recess while the cutting member axle is positioned in the groove. In a further embodiment, the one or more snap-in elements is immobilized on the drive screw by immobilizing pins, the pins preventing movement of the snap-in elements along and around the chassis.

In an additional embodiment of the present invention, the handles of the working tool are activated by grasping the handles and bringing the one or more movable handles toward a second handle substantially along the longitudinal axis (x-axis). In another embodiment, the handles are activated by grasping the handles and moving the one or more movable handles away from a second handle substantially along the longitudinal axis. Additionally, in another embodiment of the present invention, an element activates the handles of the working tool, the element being chosen from an electric motor, a hydraulic motor, a pneumatic motor and an actuator.

In another aspect of the present invention, the one or more cutting members of the working tool have a shape chosen from the following group of shapes: a concave shape, a triangular shape, a polygonal shape, an irregular shape, a saw-tooth shape, a V-shape, a square-like shape, a U-like shape, a grid-like shape and a rake-like. In another preferred embodiment of the present invention, one or more cutting members have a wire periphery circumscribing a void, the wire periphery having any of the shapes listed above.

In a preferred embodiment, the cutting member assembly of the working tool is made of a flexible material. The cutting member assembly is generally made of a material selected from one or more of the following materials: metal, polymer and composite materials.

Additionally, in a preferred embodiment of the present invention, the one or more cutting members of the working tool have dimensions of length (l) and height (h), wherein l>h. In some embodiments, the cutting member has a length of between about 3 to about 30 millimeters and a height ranging between about 1 to about 14 millimeters. In other embodiments, the cutting member has a length of between about 5 to about 13 millimeters and a height ranging between about 1 to about 6 millimeters.

Additionally in a preferred embodiment of the present invention, the one or more cutting members further include one or more forward extensions, extending from the cutting member away from the rotation mechanism. In other embodiments, the one or more cutting members further include one or more rearward extensions, extending from the cutting member toward the rotation mechanism. In yet other embodiments, the one or more cutting members further include both one or more forward extensions and one or more rearward extensions.

In yet another preferred embodiment of the present invention, the working tool further includes a cauterizing assembly. The assembly transfers energy from an energy source to the drive screw and from there to the cutting member assembly. The cutting member of the cutting member assembly thereby becomes hot and is able to resect biological tissue or coagulating blood from ruptured blood vessels by cauterization. The energy source used with the cauterizing assembly is selected from electrical, radio frequency (RF) or microwave sources or combinations thereof.

Additionally, in a preferred embodiment of the present invention, the cauterizing assembly of the working tool includes a connector connected to the energy source. It also includes a metal spring connected to the connector, and a thin metal element, where the metal element wraps around the drive screw transmitting energy from the drive screw to the cutting member axle, heating up the one or more cutting members affixed to the cutting member axle. In some embodiments, the thin metal element is formed as a sheet, a wire, or a grid-like piece of metal.

Additionally, in another aspect of the present invention, there is provided a working tool for a resectoscope for side-to-side resection of biological tissue using predetermined lateral movement. The working tool has a distal end, which is inserted into a body cavity, a proximal end that is adjacent to a user, and a longitudinal axis. The tool also includes:

a rotation mechanism which includes:
  a handle assembly located at the proximal end of the tool, the assembly including at least two handles, at least one handle being movable in the longitudinal direction of the tool; and
  a drive screw in communication via a cam element with the handle assembly, the drive screw positioned along the longitudinal axis and rotatable around that axis upon a predetermined translation of the one or more movable handles, the translation transformed to a rotation by the cam element; and
one or more cutting member assemblies positioned at the distal end of the tool, each of the one or more assemblies including:
  a cutting member axle connected by at least one connecting element to the drive screw, the cutting member axle thereby being rotatable when the drive screw rotates; and one or more cutting members connected to the cutting member axle and positioned at an end of the cutting member axle distal from the drive screw, the cutting member being operable to rotate and resect tissue to a predetermined depth in a substantially side-to-side manner upon rotation of the cutting member axle; and one or more vibrators in communication with the cutting member assembly, the one or more vibrators producing vibrations in the cutting member assembly while the cutting member is rotating, thereby abetting resection of tissue in a substantially side-to-side manner.

In yet another aspect of the present invention, there is provided a resectoscope for resecting biological tissue using lateral side-to-side motion, the resectoscope including a working tool according to any one of the above embodiments, and an optical system, the optical system affixed to the working tool, permitting viewing of the tissue being resected and viewing the cutting member of the working tool effecting the resection.

In another preferred embodiment of the resectoscope, the resectoscope further includes at least one of the following: a. an irrigation system for flushing out resected tissue from the body cavity, the irrigation system affixed to the working tool and connected to a fluid source; and b. a suction system for drawing out resected tissue from the body cavity, the suction system affixed to the working tool and connected to a suction source.

In yet another embodiment of the resectoscope, the working tool of the resectoscope further includes one or more vibrators for generating vibratory motion in the cutting member assembly of the working tool while the cutting member axle rotates. Additionally, in another embodiment of the resectoscope, the working tool of the resectoscope further includes a cauterizing assembly for imparting heat to the cutting member thereby resecting tissue and coagulating blood leaking from blood vessels ruptured during the resection.

In another aspect of the present invention, a cutting member assembly is provided which has a cutting member axle and a cutting member affixed to the cutting member axle. The cutting member of the working tool has a shape chosen from the following group of shapes: a concave shape, a triangular shape, a polygonal shape, an irregular shape, a saw-tooth shape, a V-shape, a square-like shape, a U-like shape, a grid-like shape and a rake-like shape. In another preferred embodiment of the present invention, the one or more cutting members have a wire periphery circumscribing a void, the wire periphery having any of the shapes listed above.

In a preferred embodiment, the cutting member of the cutting member assembly is made of a flexible material. The cutting member of the cutting member assembly is generally made of a material selected from one or more of the following materials: metal, polymer and composite materials.

Additionally, in a preferred embodiment of the present invention, the cutting members of the cutting member assemblies have dimensions of length (l) and height (h), wherein l>h. In another embodiment of the present invention, the dimensions of length and height can be varied.

Additionally, in a preferred embodiment of the present invention, cutting members of the cutting assemblies further include one or more forward extensions. In other embodiments, cutting members of cutting assemblies further include one or more rearward extensions. In yet other embodiments, cutting members further include both one or more forward extension and one or more rearward extensions.

In a further embodiment of the present invention, the cutting member is isolated from the environment. Additionally, in an embodiment of the invention, this isolation from the environment is effected by being at least partly coated with medical polymers or heat shrinkable, polymeric materials. In a further embodiment, the cutting member is isolated from the environment by being encased in a pouch-like member before use. In another embodiment of the present invention, the pouch-like member is formed from a plastic material.

In a further embodiment of the present invention, a flexible working tool as defined in any of the above, a flexible cutting member assembly tool as defined in any of the above and/or a flexible resectoscope comprising the same is provided.

In yet another aspect of the invention, there is provided a method for lateral resection of biological tissue including: a. inserting the distal end of a working tool of a resectoscope into a body cavity and positioning one or more cutting members of the working tool adjacent to the biological tissue to be resected; b. operating a handle assembly of the working tool, thereby imparting rotational motion to the one or more cutting members of the working tool; and c. resecting the biological tissue to a predetermined depth by using the rotational motion of the cutting member for lateral side-to-side resection of the tissue.

In yet another embodiment of the present invention, the method further includes the step of vibrating the one or more cutting members with one or more vibrators while the cutting member rotates and resects the tissue.

In an additional embodiment of the present invention, the resecting step of the method includes the step of applying heat to resect biological tissue, the heat being transferred from an energy source to the cutting member effecting the resection. In another embodiment of the method, the step of applying heat is effected after the resecting step and the resecting step is effected by rotation as above. Additionally, in this last embodiment, there may be an additional step of applying heat before the resecting step, the resecting step being effected by rotation as above.

Another embodiment of the method of the present invention further includes the step of adjusting the dimensions l and h of the cutting member, thereby controlling the depth of penetration of the cutting member.

In what has been described herein above, and what will be described herein below, the use of side-to-side and lateral have been used interchangeably. The use of one is term is intended to cover the other term as well.

BRIEF DESCRIPTION OF THE DRAWINGS

The present invention will be understood and appreciated more fully from the following detailed description taken in conjunction with the drawings in which.

Similar elements in the Figures are numbered with similar reference numerals.

DETAILED DESCRIPTION OF PREFERRED EMBODIMENTS

The present invention provides a working tool for a resectoscope useful for resection of biological tissue. The working tool of the present invention is designed to be compatible with current commercially available resectoscopes, as well as systems such as optical, suction and irrigation systems commonly used with resectoscopes. The aforementioned resectoscopes and systems of resectoscopes are readily available and may be found, for example, in the World of Endoscopy-Urology equipment catalog of Karl Storz GmbH & Co (5th edition, January 1994).

The working tool of the present invention can be used with resectoscopes which employ either electrical current, microwave energy, radio frequency (RF) energy or other sources of energy for resecting tissue and coagulating blood leaking from blood vessels ruptured during resection. Such resectoscopes will be denoted herein as "hot resectoscopes". In addition, the working tool of the present invention is useful for "cold resectoscopes" which resect biological tissue using only mechanical means. Cold resectoscopes discussed herein usually, but optionally, employ one or more vibrators for vibrating the cutting member along an axis of the working tool, typically the longitudinal axis (x-axis, see Figures herein) of the tool, while simultaneously advancing a blade-like cutting member in a rotary fashion through the tissue being resection. Optionally, a cold resectoscope can be equipped with a means for cauterization and used for coagulating blood leaking from blood vessels at the end of, or during, the resection procedure.

When the term resectoscope is used herein, the term refers to a medical device, which includes the working tool of the present invention. The tool has at least one cutting member assembly with at least one cutting member rotatable around one of the tool's axes. The resectoscope also includes an optical system, optionally an irrigation system, and optionally a suction system. Other systems may also be added to the working tool to form the complete resectoscope.

In preferred embodiments of the present invention, when the working tool is used in a cold resectoscope, the working tool generally includes one or more vibrators, which vibrate a cutting member at a predetermined amplitude along an axis of the tool, typically along the longitudinal axis (x-axis) of the tool. Typically, vibration is effected when the at least one cutting member of the at least one cutting member assembly rotates around an axis of the tool, typically the longitudinal axis. Rotation as used herein, includes the possibility of both side to side rotation or complete 360° rotation In addition, both side to side and 360° rotation are to be considered as implied when the term lateral is used.

Figure 1A:
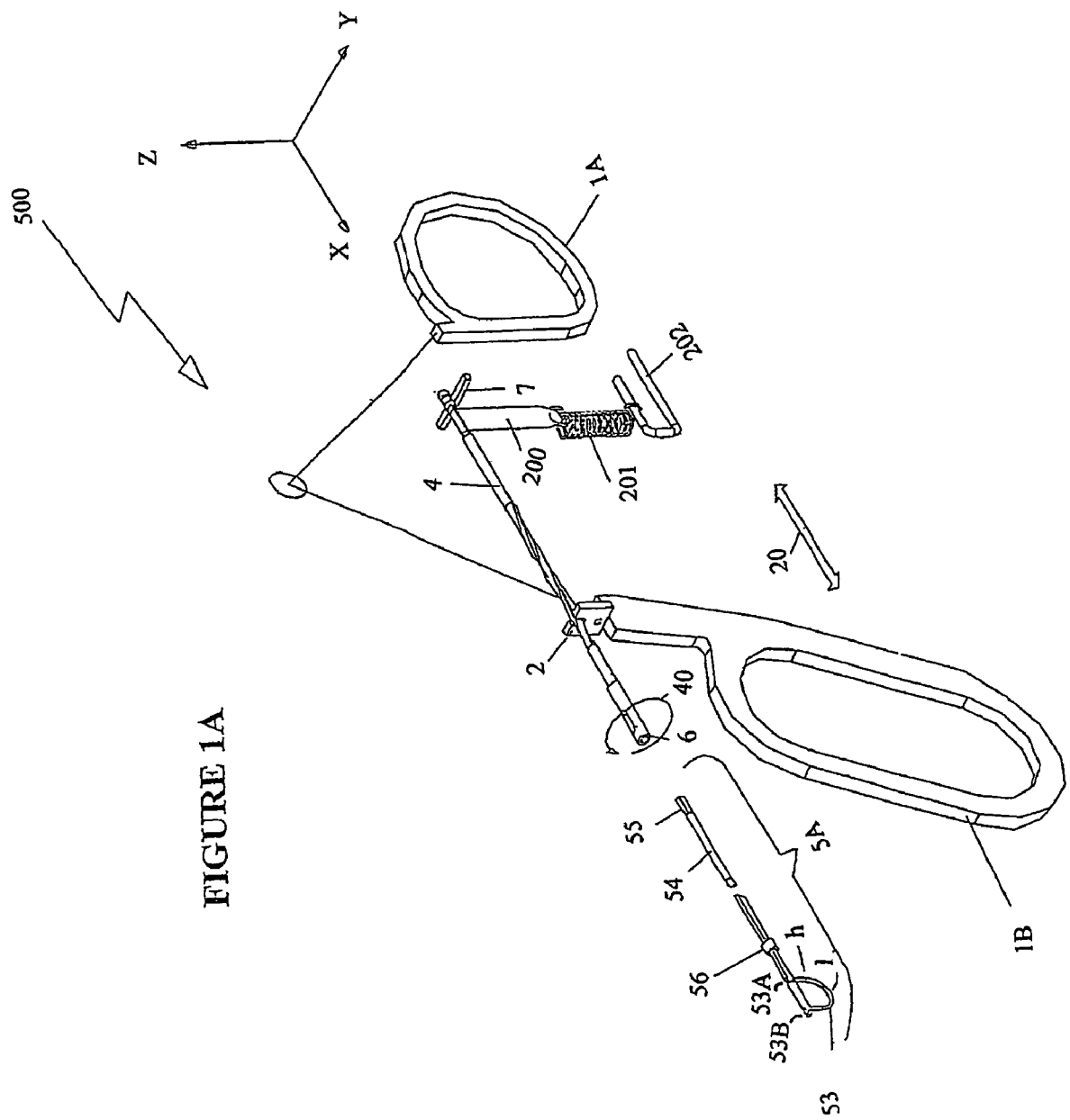
FIG. 1A is a schematic top-side view of a working tool for resectoscopes constructed in accordance with a first preferred embodiment of the present invention.
Figure 1B:
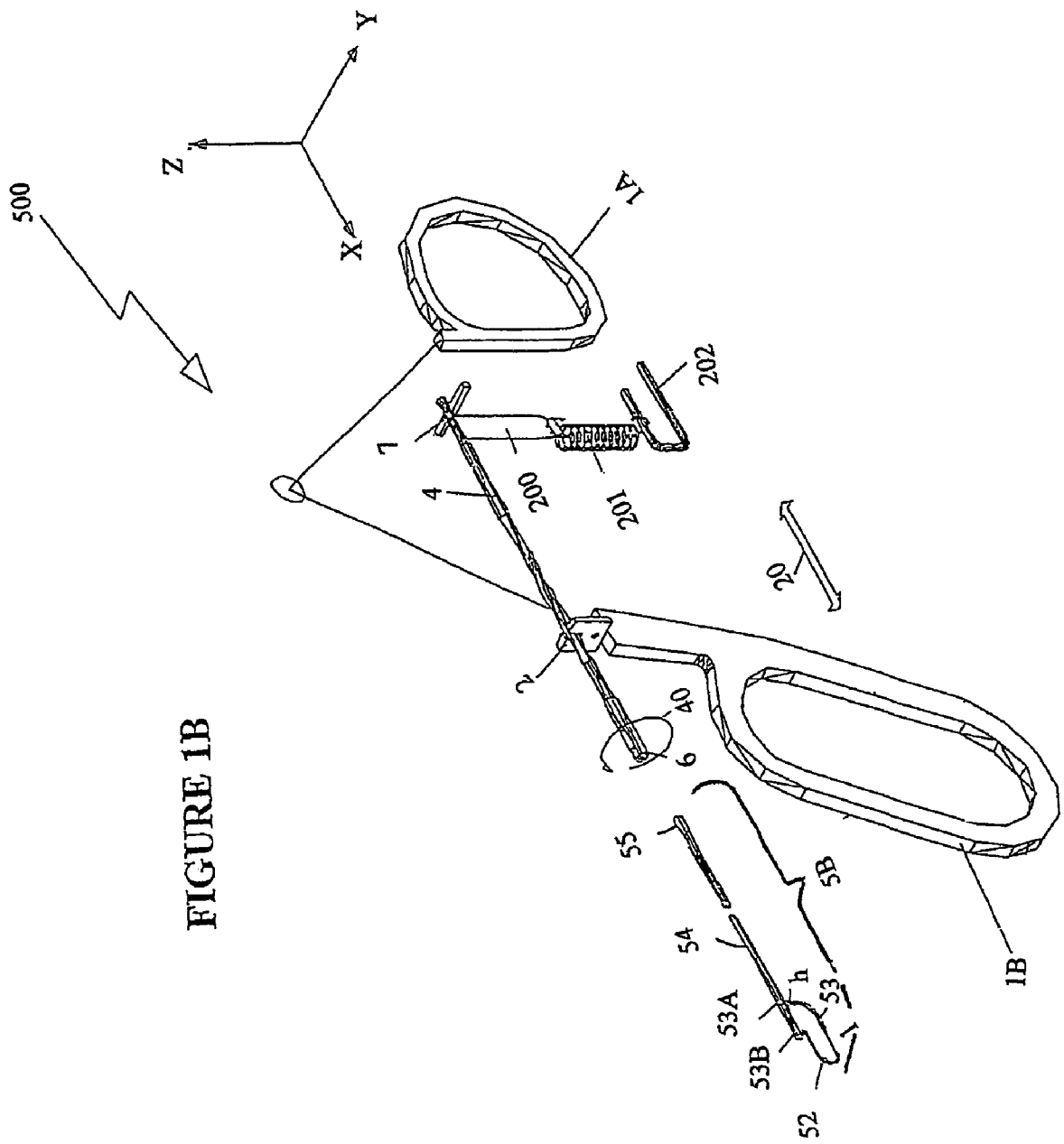
FIG. 1B is a schematic top-side view of a working tool for resectoscopes constructed in accordance with a second preferred embodiment of the present invention.

Reference is made to FIGS. 1A and 1B, which present top-side views of a working tool 500 constructed according to two preferred embodiments of the present invention. Except for the shape of the cutting member 53 as will be discussed below, both of these embodiments are identical and both are intended for use with hot resectoscopes. In these embodiments, the cutting members 53 of the cutting member assemblies 5A and 5B in FIGS. 1A and 1B respectively, are generally wire-like members lacking sharp cutting edges.

The resectoscope and/or at least a part of its ingredients may be either rigid or flexible. It is thus in the core of the present wherein the said working tool, cutting elements or a combination thereof comprising flexible materials and or made of said materials. Moreover, the term 'flexible materials' is denoted in accordance to a preferred embodiment of the present invention to a flexible working tool, cutting element or a combination thereof, wherein the term 'flexible' is denoted to any suitable equivalents selected, yet not limited to the following terms 'non-rigid', 'limber', 'elastic', 'springy' etc. Said tool and elements may comprise thus of at least homogeneous flexible composition, at least in a portion of said tool or element. Additionally or alternatively, said flexible tool or element may comprise of a plurality of hinges, joints, articulations etc.

The working tool 500 includes an assembly of handles at the tool's proximal end, including a proximal handle 1A and a distal handle 1B, wherein at least one of the handles fits the hand or finger of the user. In what is described herein, proximal relates to that part of the working tool closest to the user, while distal relates to that part of the tool closest to the tissue being resected.

When grasping and operating handles 1A and 1B, the linear movement (arrow 20) of the handles is mechanically transformed to rotational motion (arrow 40) by a drive screw 4: The threaded center section of drive screw 4 resembles a twisted rod, the cross section of which, when cut in the yz plane, appears rectangular. Drive screw 4 is locked to the device's chassis by a linear lock 7, which prevents screw 4 from traveling along the longitudinal axis (x-axis) of working tool 500.

A cam element 2 is attached either to distal handle 1B or proximal handle 1A (the latter option not shown in FIGS. 1A and 1B). Cam element 2 travels linearly along drive screw 4, thereby causing screw 4 to rotate (arrow 40) around the longitudinal axis of working tool 500. Drive screw 4 must be free to rotate to permit cam element 2 its linear travel.

Linear lock 7 is fixed at both its ends to the tool's chassis (see FIGS. 1C and 1D below) by being positioned within a groove in the tool's chassis along the y-axis. Lock 7 crosses drive screw 4 within a radial groove located in screw 4; lock 7 prevents linear travel of drive screw 4 while allowing it to rotate around the tool's longitudinal axis (x-axis).

Drive screw 4 is connected to a cutting member axle 54 having a connector 55; connector 55 is matable with a radial lock connector 6, the latter positioned at the distal end of drive screw 4, thereby linking drive screw 4 to cutting member axle 54. Because cutting member axle 54 is connected to drive screw 4 as described above, cutting member axle 54 rotates in tandem with drive screw 4 providing rotation to cutting member 53 of cutting member assembly 5A or 5B in FIGS. 1A and 1B, respectively.

Figure 1C:
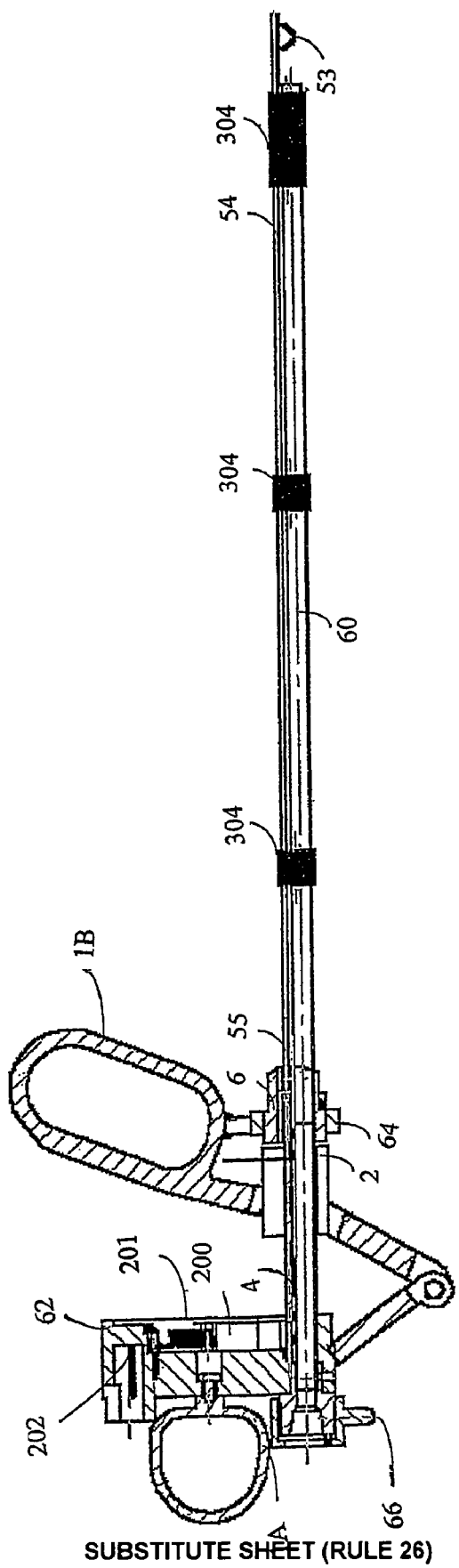
FIG. 1C is a more detailed schematic side view of a working tool for resectoscopes constructed in accordance with the embodiment of the present invention shown in FIG. 1A.
Figure 1D:
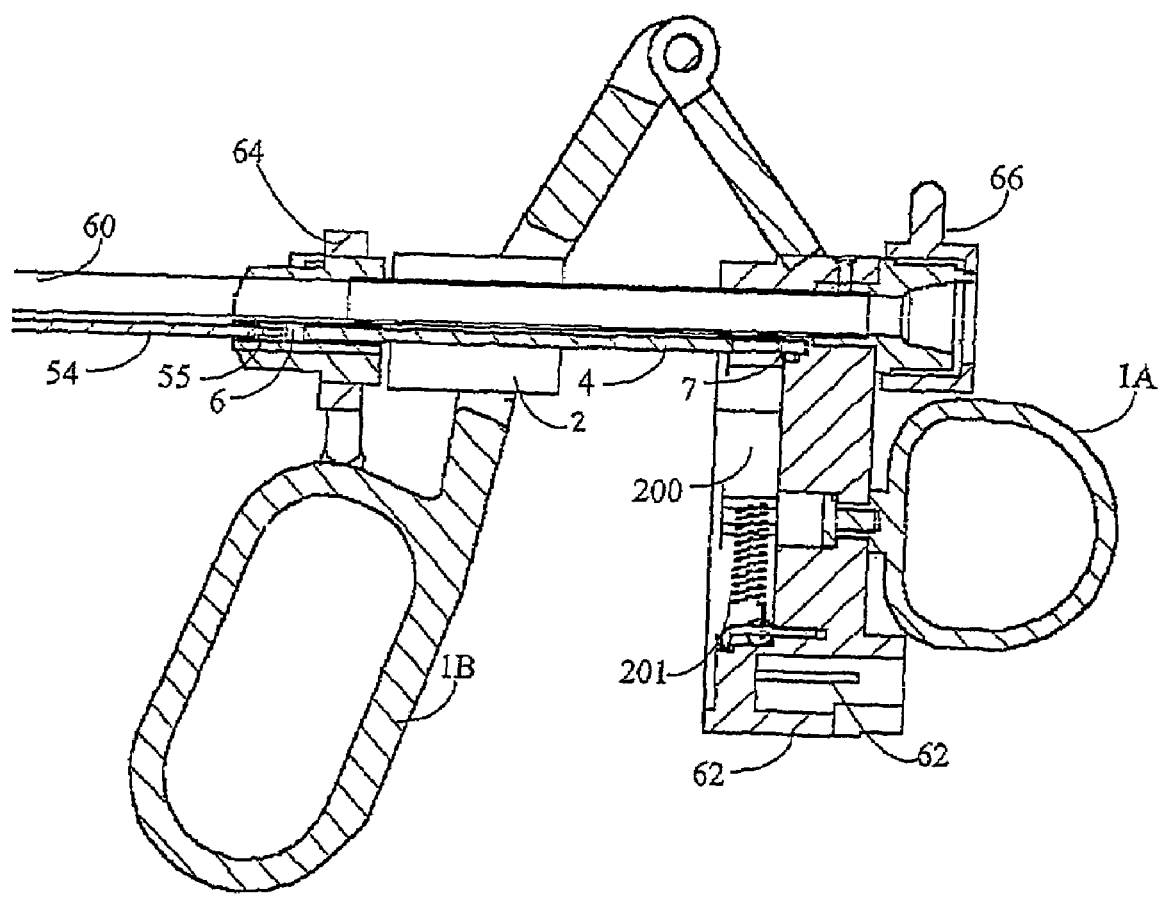
FIG. 1D is an enlarged schematic side view of the handle assembly region of the working tool shown in FIG. 1C.

In FIGS. 1A-1B, cam element 2 is shown schematically; however it can be a bolt having an aperture through which drive screw 4 is positioned, as shown in FIGS. 1C and 1D discussed herein below.

In the embodiment of FIGS. 1A and 1B, only handle 1B is mobile and handle 1A is a finger hole as will be better seen in FIGS. 1C and 1D described herein below. In other embodiments, handles 1A and 1B of the handle assembly may be arranged so that both are mobile. In yet other embodiments, one handle, for example, may be an immobilized grip support rather than a finger hole as shown as element 1A in FIGS. 1A and 1B.

According to the present invention, as schematically shown in FIGS. 1A and 1B, cutting member assemblies 5A and 5B, respectively, include, but are not limited to, at least one of the following:
(i) cutting member 53, sometimes a flexible member, which is preferably made of substances selected from metal, preferably, but not limited to, tungsten or tungsten alloys, polymer or composite materials. The member has dimensions of length (l) and height (h);
(ii) cutting member 53 is attached to cutting member axle 54 at points 53A and 53B;
(iii) connector 55, affixed at the proximal end of cutting member axle 54, having means to connect cutting member axle 54 and drive screw 4, typically by means of radial lock connector 6. Radial lock connector 6 generally possesses appropriate male or female members which are matable with corresponding female or male members on connector 55.

It should be readily apparent to one skilled in the art, that while cutting members 53 have cutting member profiles or shapes as shown in assemblies 5A and 5B of FIGS. 1A and 1B, respectively, they can readily be replaced with cutting members having other profiles or shapes. Other such profiles are illustrated in FIGS. 4A-4I described herein below. Similarly, cutting members 53 having the same profiles as those in assemblies 5A and 5B can be replaced with other cutting members 53 having different l to h ratios. Replacement is relatively simple when matable radial lock connector 6 and connector 55 described herein above are used. Furthermore, while not shown in FIGS. 1A and 1B, in some embodiments cutting members 53 (as well as the cutting members discussed below with FIGS. 4A-4I), can be configured to be attached to cutting member axle 54 at only a single point.

In addition to the elements discussed above, working tool 500 of FIGS. 1A and 1B additionally includes a means to effect resection of biological tissue and to coagulate blood leaking from blood vessels ruptured during resection using a heated cutting member. The means uses an external, non-mechanical energy source. The means transfers electric current, microwave energy, radio frequency (RF) energy or other energy from their respective sources. Typically, in the case of an electrical energy source, this transfer is effected via an electrical connector 202 located at the proximal end of working tool 500. In addition to being connected to an external energy source (not shown), electrical connector 202 is connected to a thin metal element 200, here a thin metal sheet, via a metallic spring 201. Element 200 is able to wrap itself around drive screw 4 of working tool 500 when drive screw 4 rotates. Spring 201 keeps element 200 taut as drive screw 4 rotates and ensures adequate electrical contact between element 200 and drive screw 4. An electric current flows from element 200 down drive screw 4 through cutting member axle 54 into cutting member 53. When cutting member 53 comes in contact with tissue to be resected, it heats up and cauterizes the tissue.

While connector 202 has been described above as an electrical connector, when the energy source is not electrical, for example if the energy source is an RF or microwave source, connector 202 is suitably modified to permit the energy delivered to be transferred to, and heat up, cutting member 53.

Connector 202, spring 201 and metal element 200 of FIGS. 1A and 1B comprise what is herein denoted as a cauterizing assembly. This assembly should be considered as exemplary only and not to be considered limiting. Other assemblies can be constructed which are able to transfer energy to, and heat up, cutting member 53; such other assemblies may also be used. One such assembly would use carbon brushes attached to an electrical connector 202, the latter connected to an electrical source. The carbon brushes would be in continual contact with drive screw 4, thereby transferring electricity to drive screw 4 when electricity is allowed to flow from the source. In FIGS. 1A and 1B, the cauterizing assembly is positioned between handles 1A and 1B. In other embodiments, the assembly may be positioned on the proximal side of handle 1A.

Additionally, in yet another preferred embodiment of the present invention, when elements 200, 201 and 202 are present, cold resection can be effected first without activating these elements. This can be followed by hot resection by activating and connecting these elements to the external energy source. In this, as well as other contemplated embodiments, there can be more than one cutting member assembly affixed to the resectosope's chassis. One assembly would have a wire-like cutting member suitable for hot resection while the second assembly would have a cutting member having a scalpel-like cutting edge suitable for cold resection. This two step process would be particularly effective to resect tissue with a clean cut, while additionally coagulating blood from damaged blood vessels.

Reference is now made to FIG. 1C where a more detailed side view of the working tool of FIGS. 1A and 1B are shown. The elements of the working tool in FIG. 1C found in the tools of FIGS. 1A and 1B are referenced similarly and will not be described further. FIG. 1C, additionally shows a hollow chassis 60 of the working tool and a compartment 62. Positioned within hollow chassis 60 is the optical fiber of the optical system. Compartment 62 contains the cauterizing assembly including of connector 202, spring 201 and thin metal element 200 discussed previously. Handle 1A, here a finger hole, is attached directly to compartment 62. Similarly, the axial linear lock 7 (not shown) is attached to, and immobilized within, compartment 62 as described above.

Cutting member axle 54 is attached to, and supported by, chassis 60 by snap-in elements 301. In a complete resectoscope, an optical system, an optional irrigation system and an optional suction system are inter alia positioned inside, or along the outside of, chassis 60 and brought to a region proximal to cutting member 53. The optical system is locked in position by optical lock 66, which also prevents leakage of bodily fluids from exiting the resectoscope at its proximal end. Outer tubes lock 64 holds the ancillary, often optional, systems, such as the suction and irrigation systems, in place next to, but outside, chassis 60. FIG. 1D, to which reference is now made, shows an enlarged side view of the handle assembly region of the working tool shown in FIG. 1C. Again similar parts are referenced with similar numerals and further discussion will be omitted.

Figure 2A:
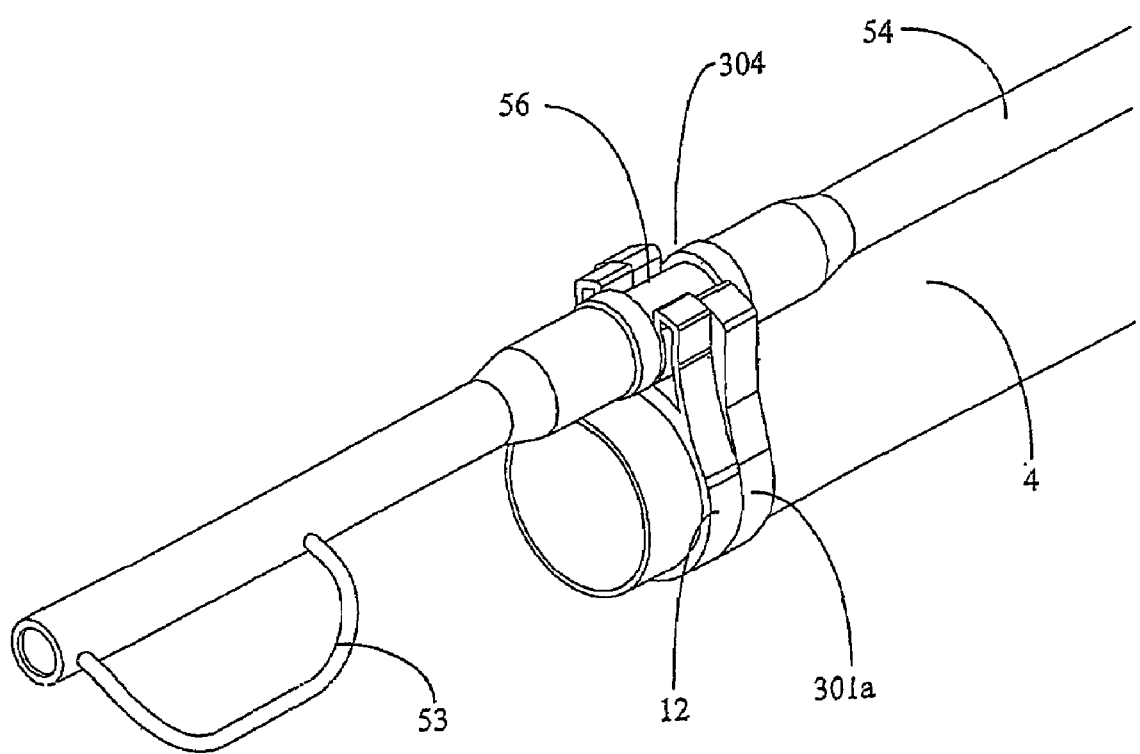
FIGS. 2A-2C are schematic isometric views of snap-in elements used with working tools constructed according to the preferred embodiments shown in FIGS. 1A-1D above and FIGS. 3A-3B below.
Figure 2B:
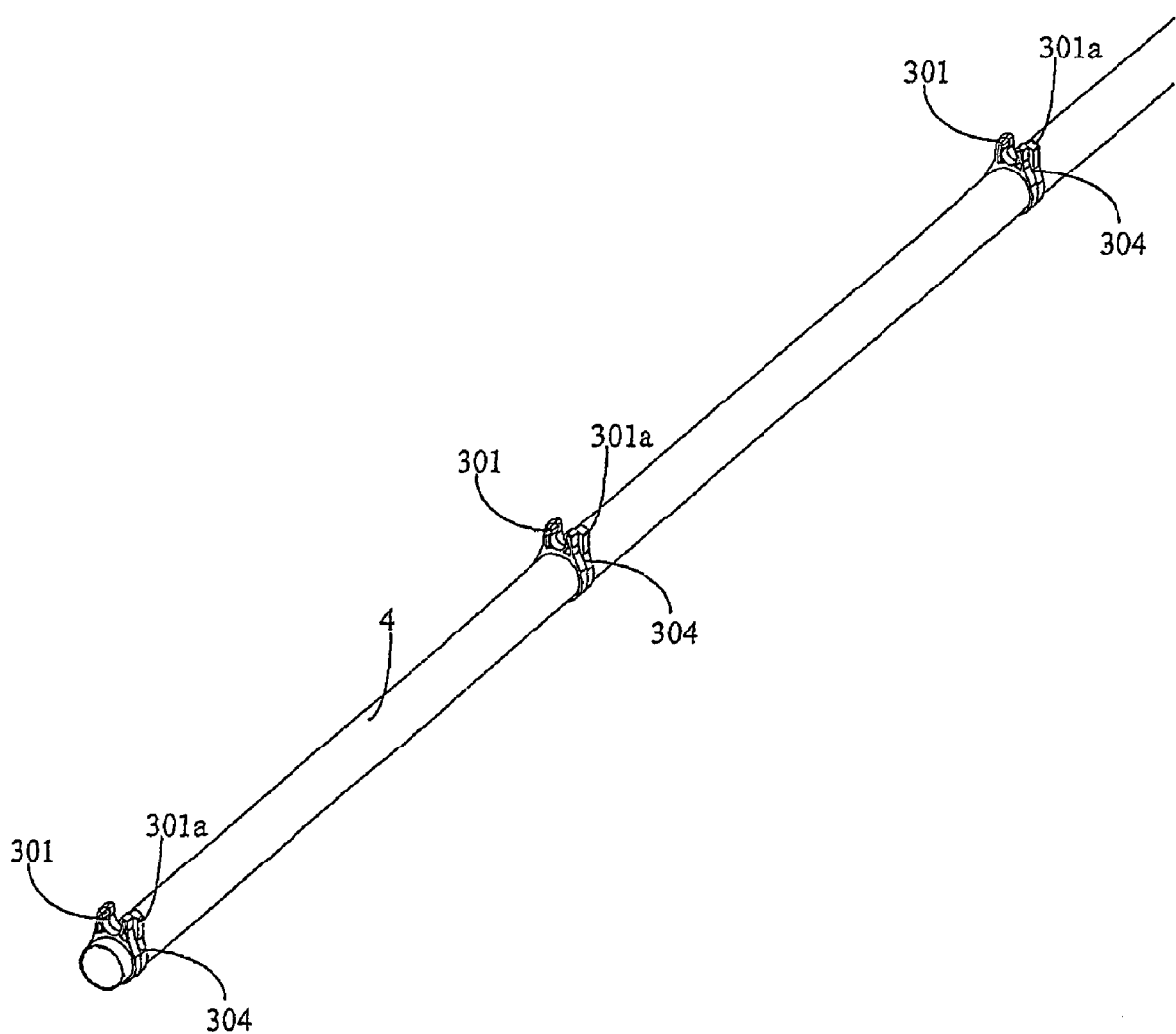
Figure 2C:
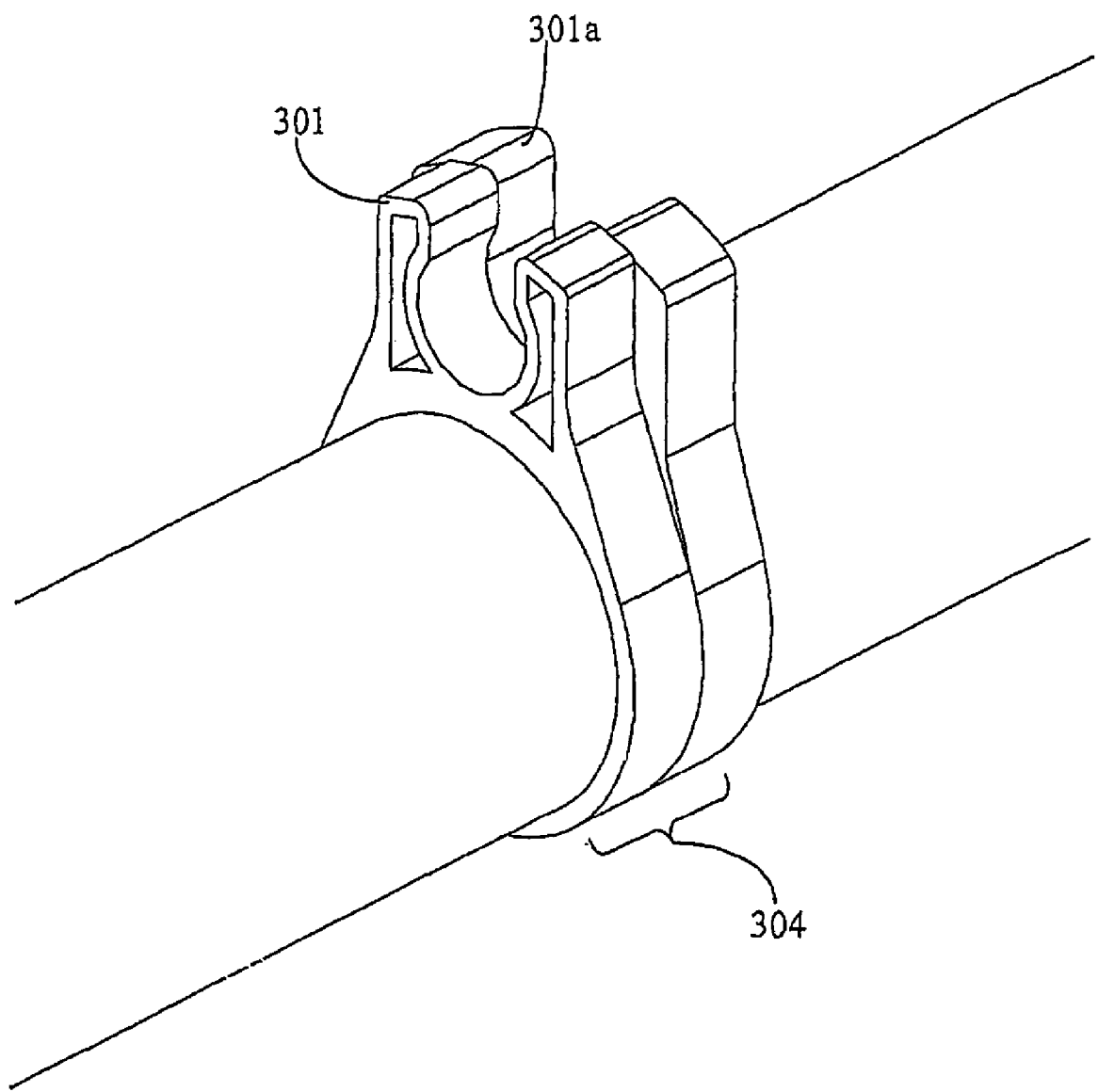
Figure 2D:
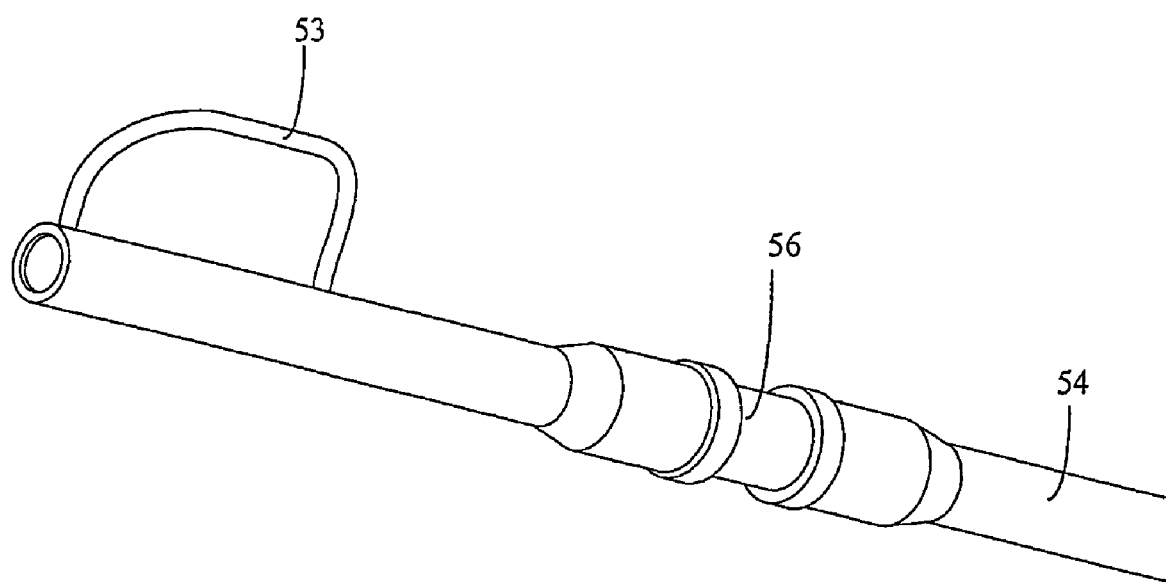
FIG. 2D is a schematic isometric view of an embodiment of a cutting member assembly used with the snap-in elements shown in FIGS. 2A-2C.

Reference is now made to FIGS. 2A-2D. FIGS. 2A-2C show different views of snap-in elements 301 used to affix cutting member axle 54 to chassis 60, the latter shown in FIGS. 1C and 1D. FIG. 2D shows a typical cutting member assembly 5C usable with the snap-in elements shown in FIGS. 2A-2C. FIGS. 2A-2C illustrate the use of snap-in elements 301, each having a groove 304 for holding a cutting member axle 54 to chassis 60. Cutting member axle 54 is positioned in grooves 304 of snap-in elements 301 and held thereto. While held by snap-in elements 301, cutting member axle 54 still has the ability to rotate around the x-axis. Cutting member 53 attached to cutting member axle 54 therefore also rotates when drive screw 4 (not shown), to which cutting member axle 54 is connected, rotates.

This is readily seen in FIG. 2A where a protruding member 56 of cutting member axle 54 fits into a possible notch-like recess of snap-in element 301, essentially locking cutting member axle 54 within snap-in elements 301 and/or 301a (one is rigid and second is flexible). In some embodiments there may be a single such snap-in element 301, while in others there may be a plurality of such snap-in elements 301 and 301a. In FIGS. 2A-2C, there is shown only a single protruding member 56 and a single notch-like recess. It should be readily apparent that other embodiments may include more than a single protruding member 56 and notch-like recess on a cutting member axle.

Immobilizing pins are possibly used according to another embodiment to hold snap-in elements 301 in a fixed position along chassis 60. Immobilizing pins or any suitable welding means in FIGS. 2A-2C are shown as being positioned parallel to the length of chassis 60. It is readily apparent to those skilled in the art that other types of snap-in elements 301 and 301a or other affixing means may also be used to affix cutting member axle 54 to chassis 60. Typical materials from which snap-in elements 301 and 301a may be constructed are various polymers or metals approved for use in medical devices. Typical polymers, which can be used, are polyetherimides (for example, Ultem 1000 sold by General Electric), polysulfones and polycarbonates among others; typical metals, which can be used, are stainless steels and titanium among others. These materials are to be considered as exemplary only and non-limiting. The other parts of the working tool may be made from any biocompatible polymers and metals. FIG. 2D shows an enlarged view of a cutting member assembly 5C having a cutting member axle 54, a cutting member 53 and a protruding member 56 which can be affixed to chassis 60 by snap-in element 301. Protruding member 56 mates with notch-like recess in snap-in element 301 of FIGS. 2A-2C. After cutting member assembly 5C is fitted into groove 304 of snap-in element 301, cutting member assembly 5C rotates when drive screw 4 (not shown) rotates. As in FIGS. 1A and 1B, cutting member axle 54 is connected to holding member axle 4 via connector 55 (not shown) on cutting member axle 54 and radial lock connector 6 (not shown) on drive screw 4 (not shown) operating as described previously. According to one embodiment of the present invention, the dimensions of cutting member 53, such as the ones shown in FIGS. 1A and 1B, are preferably characterized by l>h, where l is the length and h, the height, of cutting member 53. According to a preferred embodiment of the present invention, l is ranged between about 3 to about 30 millimeters and h is ranged between about 1 to about 14 millimeters. More preferably, l is ranged between about 5 to about 13 millimeters and h is ranged between about 1 to about 6 millimeters.

It is readily appreciated that dimension h of FIGS. 1A and 1B determines the depth of resection. The user positions the working tool's distal end adjacent, and generally parallel, to the tissue to be resected. The working tool's distal end, cutting member 53, is maintained at a predetermined distance from the essentially planar face of the tissue. Generally, the larger the value of dimension h, the deeper the resection effected inside the tissue by the working tool.

In another embodiment of the present invention, the working tool of the present invention, additionally includes a reference member (not shown), preferably, but not necessarily, located adjacent to cutting member 53. The reference member can be constructed and positioned so that it can be viewed through the resectoscope's optical system during resection, thereby assisting the user in resecting the tissue to a predetermined depth.

Figure 3A:
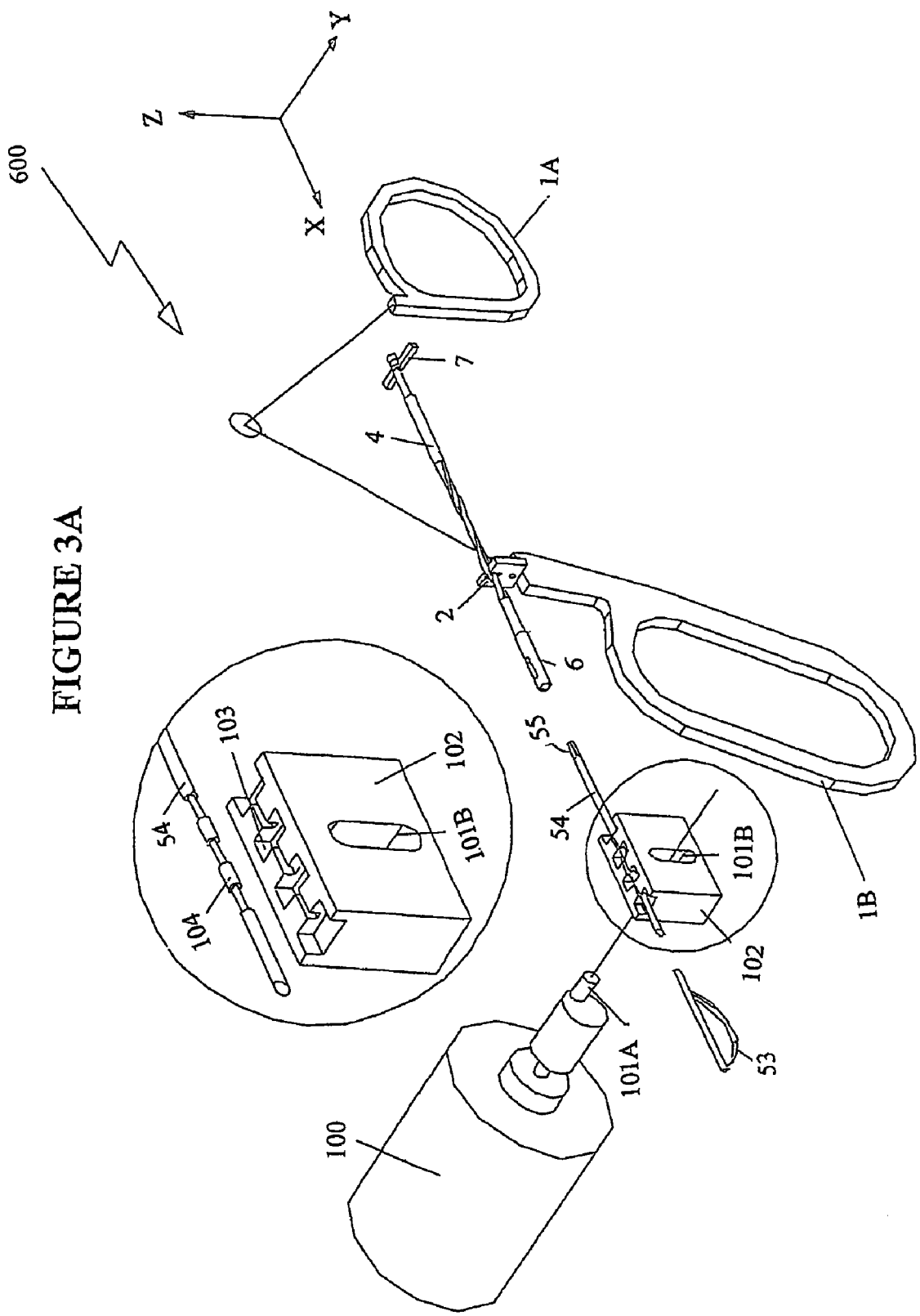
FIG. 3A is a schematic top-side view of a working tool for resectoscopes constructed in accordance with a third preferred embodiment of the present invention.

Reference is made now to FIG. 3A, which schematically presents a top-side view of a working tool 600 of a resectoscope constructed according to another preferred embodiment of the present invention. Because of the absence of a cauterizing assembly as described above, the instrument in this figure functions as a cold resectoscope. In addition to containing the elements of working tool 500 of FIGS. 1A and 1B, working tool 600 includes a vibrator to vibrate cutting member axle 54 typically back and forth along the longitudinal axis (x-axis) of tool 600. Working tool 600 includes a motor 100 having attached thereto an eccentric pin 101A. Pin 101A is positioned inside a slot 101B of a linear actuator 102. Linear actuator 102 additionally includes at least one slot-like recess 103, which is shaped and dimensioned to receive at least one male member 104 located on cutting member axle 54, thereby allowing actuator 102 to be affixed to cutting member axle 54.

Motor 100 may be selected from, but is not limited to, AC or DC electrical motors wherein the motor is in connection with a power source which may be selected from at least one rechargeable battery, at least one non-rechargeable battery, or a central electrical supply. Pneumatic motors, typically those comprising at least one vibrating piston actuated by gas flow, may also be used. The pneumatic generator for the pneumatic motor is preferably located at the proximal end of the working tool, or alternatively is positioned separately from the working tool, and is in communication with an actuator by a narrow connecting tube. Finally, hydraulic motors may also be used.

Motor 100 and linear actuator 102 of working tool 600 typically generate vibratory motion back and forth along the longitudinal axis (x-axis) of working tool 600 while cutting member 53 rotates or oscillates around the x-axis. This rotation or oscillation allows resection from a lateral side-to-side direction. Cutting member 53 of working tool 600 of the resectoscope rotates or oscillates from side-to-side at a predetermined depth. Generally, the depth is determined by dimension h (see FIGS. 1A and 1B) of cutting member 53.

In what is described herein, it is readily understood that lateral (side-to-side) motion describes motion around the ±x-axis. Additionally, the vibrator shown in FIGS. 3A-3B vibrates the cutting member axle substantially back and forth along the ±x-axis.

Figure 3B:
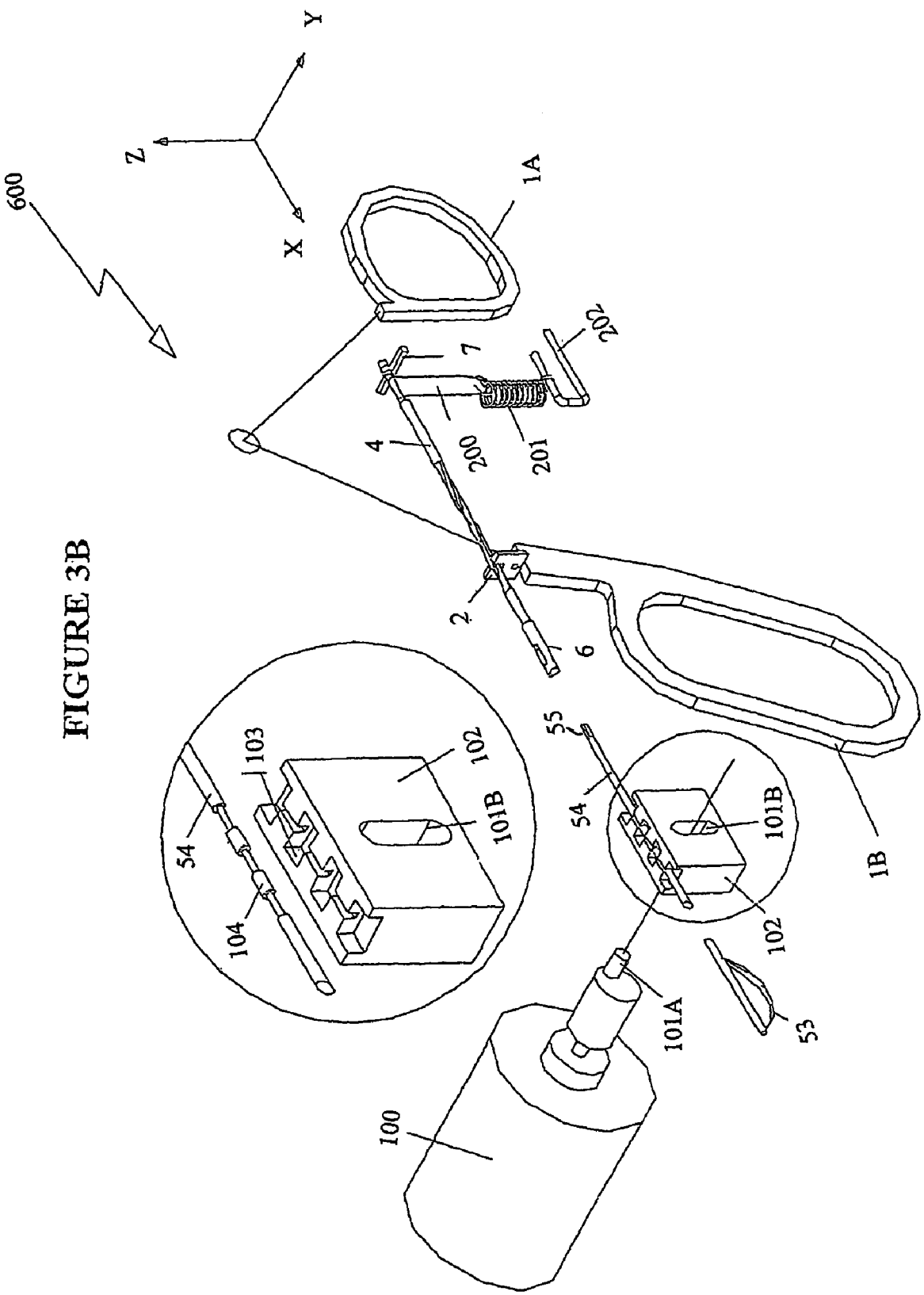
FIG. 3B is a schematic top-side view of a working tool for resectoscopes constructed in accordance with a fourth preferred embodiment of the present invention.

It should readily be understood by one skilled in the art that any suitable vibrator, which can generate vibrations along cutting member axle 54, may be used instead of a vibrator such as the one shown in FIGS. 3A-3B. Such vibrators include, for example, an electromagnet, which periodically attracts and repels axle 54. Similarly, an ultrasound actuator affixed to cutting member axle 54 may also be used. Additionally, several types of electrical vibrators, such as crystal and piezoelectric oscillators, may also be used.

FIG. 3B, to which reference is now made, shows a top-side view of a working tool in another embodiment of the invention. In all respects, it is the same as the embodiment discussed with FIG. 3A except that additionally it includes a cauterizing assembly with which to coagulate blood leaking from blood vessels ruptured during resection. Typically, cauterization of the blood vessels here is done at the end of and/or during the surgical procedure.

The embodiment in FIG. 3B operates as a cold resectoscope, excising diseased or suspect tissue mechanically, generally with the added assistance of a vibrator, using a cutting member having a sharp cutting edge. Such cutting members will be described herein below with FIGS. 4A-4I. The cauterizing assembly shown in FIG. 3B is constructed and operated in a manner identical to the one discussed with FIGS. 1A-1B and will not be further discussed here.

In other embodiments, the working tool in FIG. 3B can also be used first as a cold resectoscope, generally with the aid of the vibrator, and then as a hot resectoscope where it completes tissue resection and cauterizes ruptured blood vessels. Alternatively, it can begin a resection operating as a hot resectoscope, without the use of the vibrator, employing only rotation and cauterization while resecting the tissue. The working tool can then complete the resection as a cold resectoscope without cauterization, using rotation, with or without vibration. In yet other resections, the working tool in FIG. 3B can first be operated as a hot resectoscope, using rotation without vibration, then as a cold resectoscope using rotation and vibration, and then again as a hot resectoscope using rotation without vibration. In such a case, there is reduced bleeding while the resected tissue is minimally damaged, remaining usable for biopsies. This minimal damage includes even the deepest portions of the resected tissue. It is readily understood that in these last embodiments, the scalpel-like blade required for cold resectoscopes as described herein below, can also act as a hot wire when used as a cutting member in hot resectoscopes.

Figure 3C:
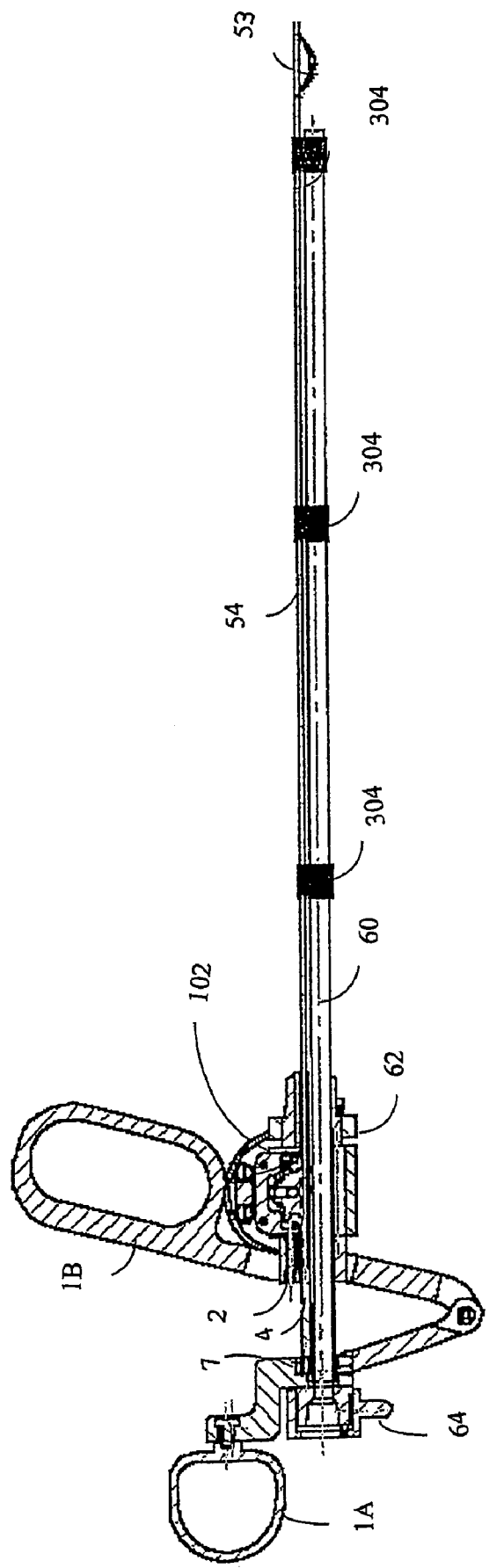
FIG. 3C is a more detailed schematic side view of a working tool for resectoscopes constructed in accordance with the embodiment of the present invention shown in FIG. 3A.
Figure 3D:
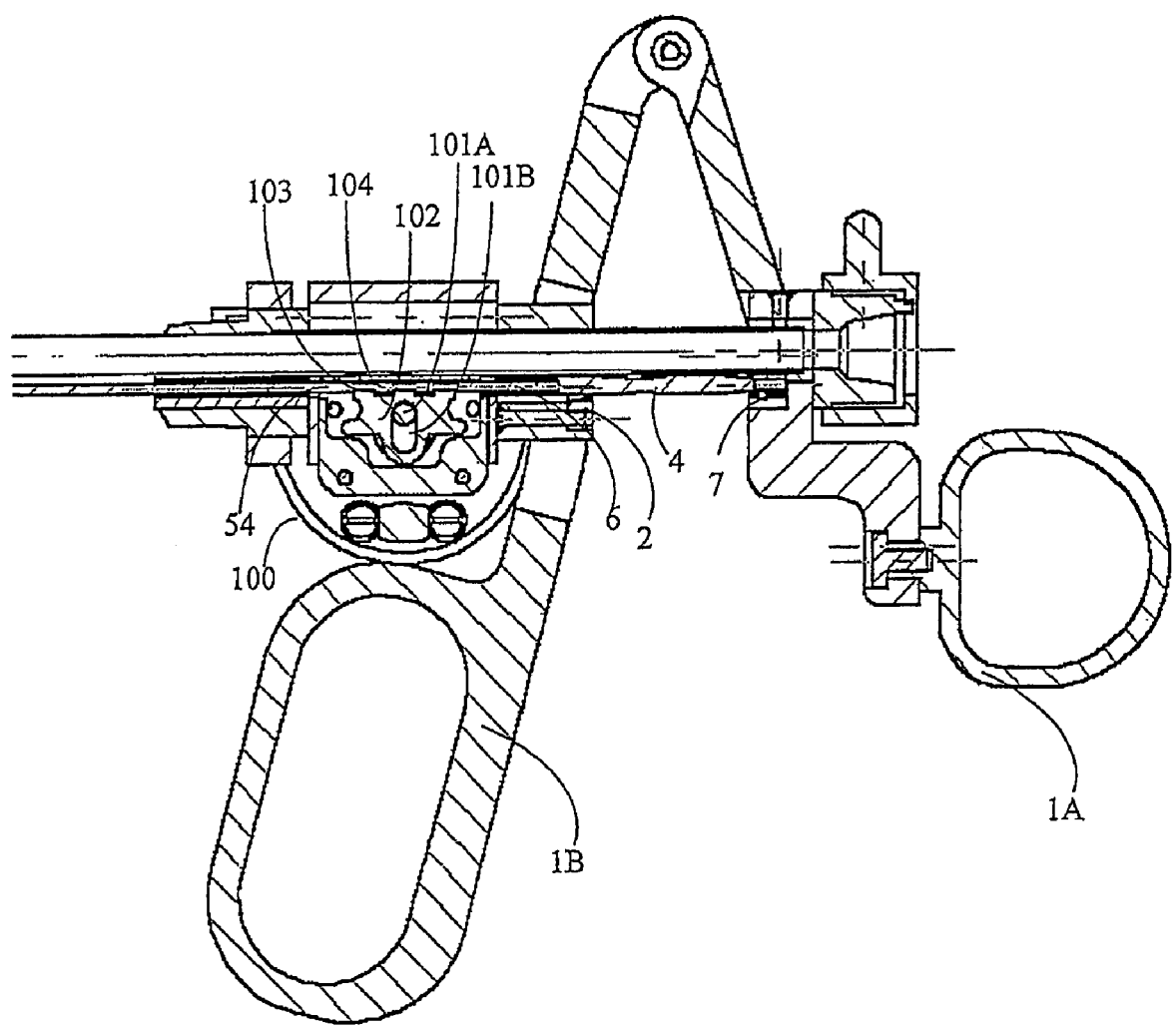
FIG. 3D is an enlarged schematic side view of the handle assembly region of the working tool shown in FIG. 3C.
Figure 3E:
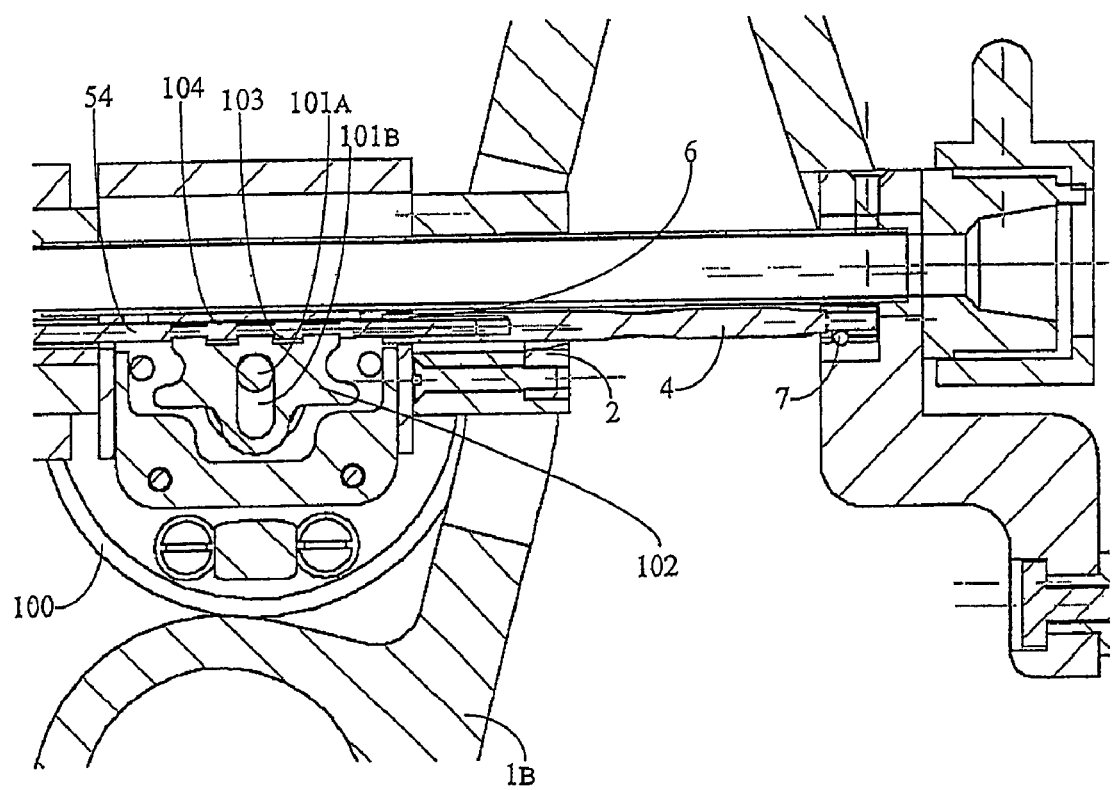
FIG. 3E is a further enlarged schematic side view of the handle assembly region of the working tool shown in FIG. 3D.

Reference is now made to FIGS. 3C-3E, which show progressively more detailed side views of the embodiment in FIG. 3A. FIGS. 3D-3E concentrate on the handle assembly region of the working tool. FIG. 3C shows chassis 60, outer tubes lock 62 and optical lock 64, the purpose and operation of which have been described with FIG. 1C and will not be remarked on further. FIGS. 3D-3E show more detail of the handle region and show the attachment of motor 100 to linear actuator 102 with eccentric pin 101A through slot 101B. Also shown are male members 104 and slot-like recess 103, discussed previously with FIG. 3A.

It should be readily understood by one skilled in the art that the invention allows for an embodiment wherein the working tool in a cold resectoscope is similar to the one shown in FIG. 3A but without the vibrator, i.e. motor 100 and linear actuator 102. Such a tool would resect tissue solely by rotation of the cutting member. The cutting member would require a sharp scalpel-like cutting edge. The rotation and other aspects of the operation of such a working tool has been described above with FIGS. 1A-1B.

Figure 4A:
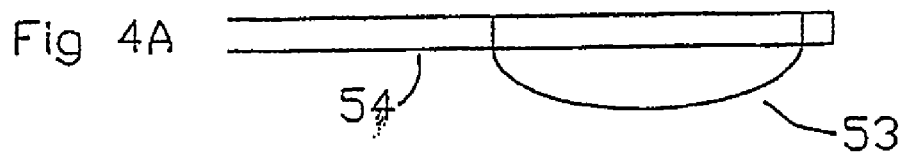
FIGS. 4A-4I are schematic side and isometric views of various cutting member assemblies used with preferred embodiments of the present invention.
Figure 4B:
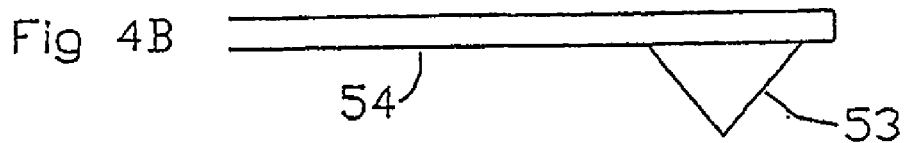
Figure 4C:
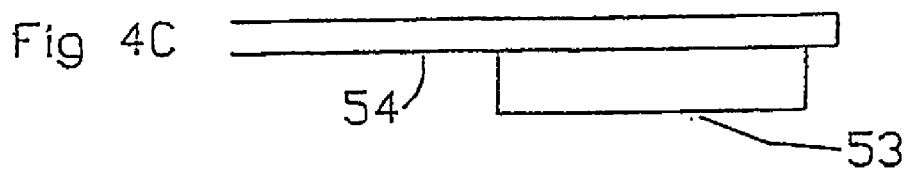
Figure 4D:
Figure 4E:
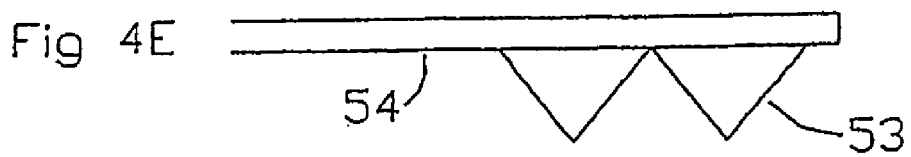
Figure 4F:
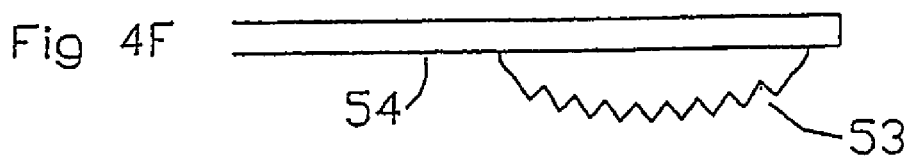
Figure 4G:
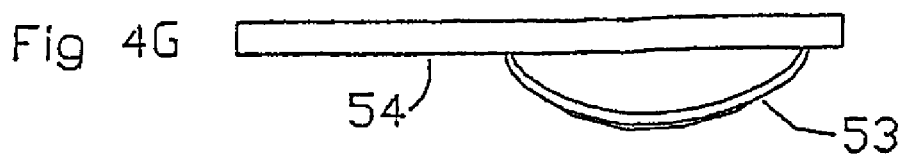
Figure 4H:
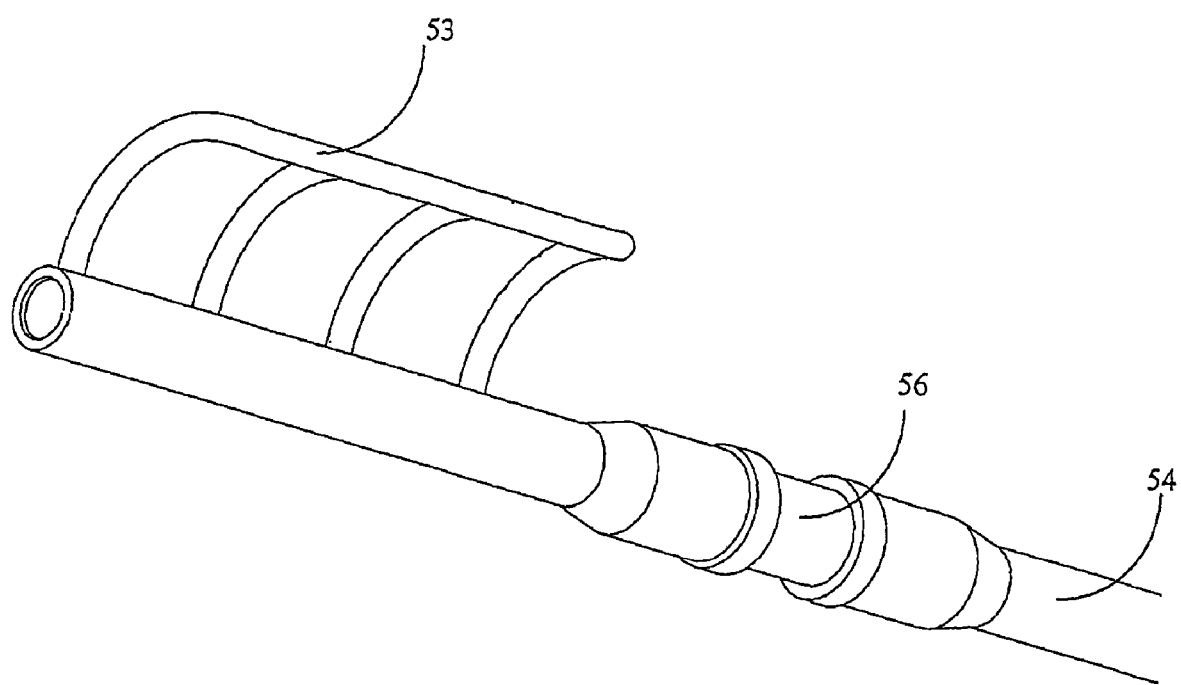
Figure 4I:
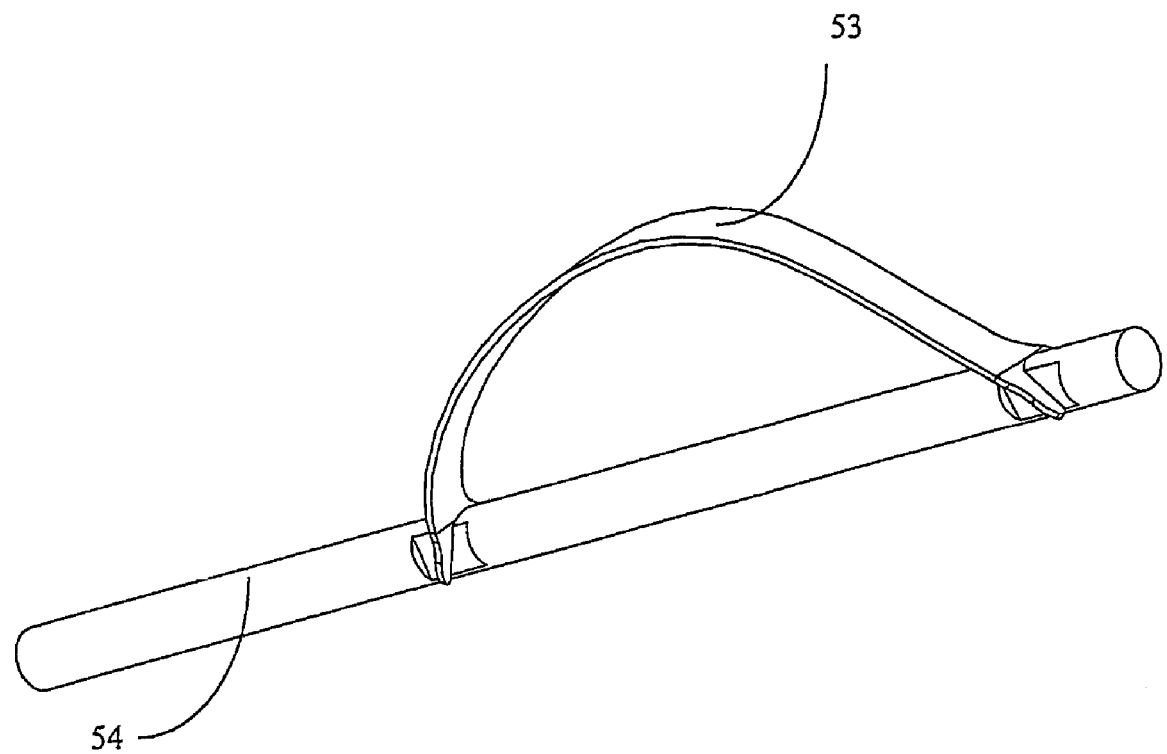

It is also contemplated that within the scope of the present invention and in accordance with FIGS. 4A-4I to which reference is now made, the cutting members 53 may have any of the following profiles or shapes: a concave shape (FIG. 4A), a triangular shape (FIG. 4B), a square shape (FIG. 4C), a polygonal shape (not shown), an irregular shape (FIG. 4D), a V-shape (FIG. 4E), a saw-tooth shape (FIG. 4F), a spoon-like shape (FIG. 4G), a grid-like shape (not shown), and a rake-like shape (FIG. 4H). The rake-like structure in FIG. 4H is curved with its prongs joined at their ends distal from their points of attachment to cutting member axle 54. The rake-like structure in FIG. 4H is particularly preferred for prostrate resections. FIG. 4I shows a particularly useful shape for use with cold resectoscopes. The cutting member in FIG. 4I has a well-defined scoop-like shape with sharp cutting edges. It should be evident to one skilled in the art that the above shapes are to be viewed as exemplary only and non-limiting. Other shapes can also be used provided that they are suitable for resecting the tissue being excised. It should also be readily apparent to one skilled in the art that certain shapes are more preferable for resections with certain tissue and less preferable with others.

Cutting members 53 of FIGS. 4A-4I can resect tissue by using mechanical, electrical, radio frequency and microwave means as discussed above or any combination thereof, i.e. they can be used with cold or hot resectoscopes. In general, when used in mechanical resectoscopes, i.e. cold resectoscopes, the wire periphery of the cutting member must have a scalpel-like cutting edge. Such an edge is not required when a hot resectoscope is used. One particularly preferred cutting member shape for cold resectoscopes is the spoon-like shape of FIG. 4G, which has a cutting edge and the cutting characteristics of clinically utilized scalpels.

According to another preferred embodiment of the present invention, as schematically presented in FIG. 4D, the cutting member 53 further includes a forward extension 52, useful for frontal resection of biological tissue. Additionally or alternatively, a sideward or rearward extension (not shown) in various shapes and sizes may be employed in resecting biological tissue. Furthermore both a forward and a rearward extension can be formed on, and used with, a single cutting member.

It is within the scope of the present invention to isolate at least part of the cutting members from the environment. This can be effected by any of various methods known in the art, such as by coating the cutting members with medical grade polymers, by covering at least part of the cutting members with heat-shrinkable polymeric materials, or by using other such isolating materials and methods. In one particularly preferred embodiment of the present invention, the cutting member is encased in a pouch-like member for at least part of the time, preferably before inserting and after withdrawing the resectoscope into and from the body cavity. Preferably, the pouch-like member is made of plastic materials, which isolate the cutting member from other metallic materials of the working tool.

While in some embodiments the dimensions l and h are constant for a given cutting member, in other embodiments cutting members 53 can be constructed so that the ratio of l to h (see FIG. 1A) is variable allowing a single cutting member 53 to resect at various predetermined depths. When cutting member 53 has a wire construction, this can be effected by having several attachment points along cutting member axle 54 which would shorten or lengthen l and h. It should be readily apparent to one skilled in the art that other methods for varying the dimensions of a given cutting member may also be used.

It will be appreciated by persons skilled in the art that the present invention is not limited by what has been particularly shown and described herein above. Rather the scope of the invention is defined by the claims that follow.

The invention claimed is:

1. A working tool for a resectoscope for side-to-side resection of biological tissue using determined lateral movement, said working tool having a distal end which is inserted into a body cavity, a proximal end which is adjacent to a user, and a longitudinal axis, and wherein said tool includes:
   a rotation mechanism which includes;
   a handle assembly located at said proximal end of said tool, which includes at least two handles, at least one handle being movable in the longitudinal direction of the tool;
   a drive screw in communication via a cam element with said handle assembly, said drive screw positioned along the longitudinal axis and rotatable there around upon a predetermined translation of said at least one movable handle, the translation transformed to a rotation by said cam element; the drive screw is anchored within said working tool by at least one linear lock, which prevents said screw from traveling along the longitudinal axis (x-axis) of working tool, allowing it to rotate around said axis; said cam element travels linearly along said drive screw, thereby causing said drive screw to rotate around the longitudinal axis of said working tool;
   at least one cutting member assembly positioned at said distal end of said tool, and each of said at least one assembly includes: a cutting member axle connected by at least one connecting element to said drive screw, said cutting member axle thereby being rotatable upon rotation of said drive screw;
   and at least one cutting member connected to said cutting member axle and positioned at an end of said cutting member axle distal from said drive screw, said cutting member, when held in a determined position with respect to tissue to be resected, being operable to rotate and resect tissue to a predetermined depth in a substantially side-to-side manner upon rotation of said cutting member axles,
wherein a chassis of said working tool is fitted with at least one snap-in element positioned along said chassis's length, and wherein said cutting member axle is positioned and held within said at least one snap-in element while being free to rotate around the tool's longitudinal axis (x-axis).

2. A working tool according to claim 1, wherein said at least one snap-in element comprises a groove with a female notch-like recess and said cutting member axle comprises a male protruding member, said protruding member being adapted for mating with the groove's female notch-like recess while said cutting member axle is positioned in said groove.

3. A working tool according to claim 1, wherein said at least one snap-in element is fixed on said drive screw by fixing pins, which prevent movement of said snap-in element along and around said chassis.

4. A working tool for a resectoscope for side-to-side resection of biological tissue using determined lateral movement, said working tool having a distal end which is inserted into a body cavity, a proximal end which is adjacent to a user, and a longitudinal axis, and wherein said tool includes:
   a rotation mechanism which includes;
   a handle assembly located at said proximal end of said tool, which includes at least two handles, at least one handle being movable in the longitudinal direction of the tool;
   a drive screw in communication via a cam element with said handle assembly, said drive screw positioned along the longitudinal axis and rotatable there around upon a predetermined translation of said at least one movable handle, the translation transformed to a rotation by said cam element; the drive screw is anchored within said working tool by at least one linear lock, which prevents said screw from traveling along the longitudinal axis (x-axis) of working tool, allowing it to rotate around said axis; said cam element travels linearly along said drive screw, thereby causing said drive screw to rotate around the longitudinal axis of said working tool;
   at least one cutting member assembly positioned at said distal end of said tool, and each of said at least one assembly includes: a cutting member axle connected by at least one connecting element to said drive screw, said cutting member axle thereby being rotatable upon rotation of said drive screw;
   at least one cutting member connected to said cutting member axle and positioned at an end of said cutting member axle distal from said drive screw, said cutting member, when held in a determined position with respect to tissue to be resected, being operable to rotate and resect tissue to a predetermined depth in a substantially side-to-side manner upon rotation of said cutting member axle, and
   at least one vibrator, said at least one vibrator comprising a motor which further includes an eccentric pin positionable in a slot in a linear actuator and affixed thereto, and wherein said linear actuator additionally includes at least one female slot-like recess, which is spaced and dimensioned to fit at least one male member located on said cutting member axle, thereby affixing said actuator to said cutting member axle.

5. A working tool according to claim 4, wherein said motor is selected from a group consisting of an AC electrical motor, a DC electrical motor, a hydraulic motor, and a pneumatic motor.

6. A working tool for a resectoscope for side-to-side resection of biological tissue using determined lateral movement, said working tool having a distal end which is inserted into a body cavity, a proximal end which is adjacent to a user, and a longitudinal axis, and wherein said tool includes:
   a rotation mechanism which includes;
   a handle assembly located at said proximal end of said tool, which includes at least two handles, at least one handle being movable in the longitudinal direction of the tool;
   a drive screw in communication via a cam element with said handle assembly, said drive screw positioned along axis and rotatable there around upon a predetermined translation of said at least one movable handle, the translation transformed to a rotation by said cam element; the drive screw is anchored within said working tool by at least one linear lock, which prevents said screw from traveling along the longitudinal axis (x-axis) of working tool, allowing it to rotate around said axis; said cam element travels linearly along said drive screw, thereby causing said drive screw to rotate around the longitudinal axis of said working tool;
   least one cutting member assembly positioned at said distal end of said tool, and each of said at least one assembly includes: a cutting member axle connected by at least one connecting element to said drive screw, said cutting member axle thereby being rotatable upon rotation of said drive screw;
   and at least one cutting member connected to said cutting member axle and positioned at an end of said cutting member axle distal from said drive screw, said cutting member, when held in a determined position with respect to tissue to be resected, being operable to rotate and resect tissue to a predetermined depth in a substantially side-to-side manner upon rotation of sad cutting member axle, wherein a chassis of said working tool is fitted with at least one snap-in element positioned along said chassis's length, and wherein said cutting member axle is positioned and held within said at least one snap-in element while being free to rotate around the tool's longitudinal axis (x-axis) and translate along the longitudinal axis.

* * * * *